(12) United States Patent
West et al.

(10) Patent No.: US 7,400,755 B2
(45) Date of Patent: Jul. 15, 2008

(54) INVERSE PLANNING USING OPTIMIZATION CONSTRAINTS DERIVED FROM IMAGE INTENSITY

(75) Inventors: Jay B. West, Mountain View, CA (US); Michael J. Saracen, Oakland, CA (US); John R. Dooley, Castro Valley, CA (US)

(73) Assignee: Accuray Incorporated, Sunnyvale, CA (US)

( * ) Notice: Subject to any disclaimer, the term of this patent is extended or adjusted under 35 U.S.C. 154(b) by 321 days.

(21) Appl. No.: 11/144,235

(22) Filed: Jun. 2, 2005

(65) Prior Publication Data

US 2006/0274924 A1  Dec. 7, 2006

(51) Int. Cl.
*G06K 9/00* (2006.01)
(52) U.S. Cl. .................. 382/128; 382/130; 382/131; 382/132
(58) Field of Classification Search .............. 382/128, 382/132, 219, 274, 278; 128/922, 923
See application file for complete search history.

(56) References Cited

U.S. PATENT DOCUMENTS

| | | | | |
|---|---|---|---|---|
| 5,247,555 | A | | 9/1993 | Moore et al. |
| 5,537,485 | A | * | 7/1996 | Nishikawa et al. .......... 382/130 |
| 5,579,360 | A | | 11/1996 | Abdel-Mottaleb |
| 5,638,458 | A | * | 6/1997 | Giger et al. ................. 382/132 |
| 5,657,362 | A | * | 8/1997 | Giger et al. .................. 378/37 |
| 5,947,981 | A | * | 9/1999 | Cosman ...................... 606/130 |
| 6,075,879 | A | * | 6/2000 | Roehrig et al. .............. 382/132 |
| 6,081,739 | A | * | 6/2000 | Lemchen ..................... 600/407 |
| 6,143,003 | A | | 11/2000 | Cosman |
| 6,317,617 | B1 | * | 11/2001 | Gilhuijs et al. .............. 600/408 |
| 6,405,072 | B1 | * | 6/2002 | Cosman ...................... 600/426 |
| 6,662,036 | B2 | * | 12/2003 | Cosman ...................... 600/411 |
| 6,748,347 | B1 | * | 6/2004 | Dalton .......................... 703/5 |

OTHER PUBLICATIONS

Ling, C. Clifton, et al., Towards Multidimensional Radiotherapy (MD-CRT): Biological Imaging and Biological Conformality Copyright 2000 Elsevier Science Inc. Int. J. Radiation Oncology Biol. Phys. vol. 47, No. 3, pp. 551-560.

Maintz, J.B. Antoine, et al., "A Survey of Medical Image Registration" Received May 25, 1997, revised Oct. 10, 1997, accepted Oct. 16, 1997, Image Sciences Institute, Utrecht University Hospital, Utrecht, the Netherlands. Copyright Oxford University Press, pp. 1-37.

PCT International Search Report, PCT/US06/21578 filed Jun. 1, 2006, mailed Sep. 26, 2007.

PCT Written Opinion of the International Searching Authority, PCT/US06/21578 filed Jun. 1, 2006, mailed Sep. 25, 2007.

PCT Preliminary Report on Patentability (Chapter I of the Patent Cooperation Treaty), PCT/US2006/021578 filed Jun. 1, 2006, mailed Dec. 6, 2007.

* cited by examiner

*Primary Examiner*—Yosef Kassa
(74) *Attorney, Agent, or Firm*—Blakely, Sokoloff, Taylor & Zafman, LLP

(57) ABSTRACT

A method of automatically identifying a region of differing intensity in a functional image is described.

4 Claims, 12 Drawing Sheets

INVERSE PLANNING USING OPTIMIZATION CONSTRAINTS DERIVED FROM IMAGE INTENSITY

TECHNICAL FIELD

This invention relates to the field of radiation treatment, and in particular, to inverse planning in radiation treatment.

BACKGROUND

Tumors and lesions are types of pathological anatomies characterized by abnormal growth of tissue resulting from the uncontrolled, progressive multiplication of cells, while serving no physiological function.

A non-invasive method for pathological anatomy treatment is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source is changed, every beam passes through the tumor site, but passes through a different area of healthy tissue on its way to the tumor. As a result, the cumulative radiation dose at the tumor is high and the average radiation dose to healthy tissue is low. The term radiotherapy refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centi-Grays (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted by the magnitude of the radiation.

Conventional isocentered radiosurgery systems (e.g., the Gamma Knife) use forward treatment planning. That is, a medical physicist determines the radiation dose to be applied to a tumor and then calculates how much radiation will be absorbed by critical structures and other healthy tissue. There is no independent control of the two dose levels, for a given number of beams, because the volumetric energy density at any given distance from the isocenter is a constant, no matter where the isocenter is located.

Inverse planning, in contrast to forward planning, allows the medical physicist to independently specify the minimum tumor dose and the maximum dose to other healthy tissues, and lets the treatment planning software select the direction, distance, and total number and energy of the beams. Conventional treatment planning software packages are designed to import 3-D images from a diagnostic imaging source, for example, computerized x-ray tomography (CT) scans. CT is able to provide an accurate three-dimensional model of a volume of interest (e.g., skull or other tumor bearing portion of the body) generated from a collection of CT slices and, thereby, the volume requiring treatment can be visualized in three dimensions.

During inverse planning, a volume of interest (VOI) is used to delineate structures to be targeted or avoided with respect to the administered radiation dose. That is, the radiation source is positioned in a sequence calculated to localize the radiation dose into a VOI that as closely as possible conforms to the tumor requiring treatment, while avoiding exposure of nearby healthy tissue. Once the target (e.g., tumor) VOI has been defined, and the critical and soft tissue volumes have been specified, the responsible radiation oncologist or medical physicist specifies the minimum radiation dose to the target VOI and the maximum dose to normal and critical healthy tissue. The software then produces the inverse treatment plan, relying on the positional capabilities of the radiation treatment system, to meet the min/max dose constraints of the treatment plan.

The two principal requirements for an effective radiation treatment system are conformality and homogeneity. Homogeneity is the uniformity of the radiation dose over the volume of the target (e.g., pathological anatomy such as a tumor, lesion, vascular malformation, etc.) characterized by a dose volume histogram (DVH). An ideal DVH would be a rectangular function, where the dose is 100 percent of the prescribed dose over the volume of the tumor and zero elsewhere.

Conformality is the degree to which the radiation dose matches (conforms) to the shape and extent of the target (e.g., tumor) in order to avoid damage to critical adjacent structures. More specifically, conformality is a measure of the amount of prescription (Rx) dose (amount of dose applied) within a target VOI. Conformality may be measured using a conformality index (CI)=total volume at >=Rx dose/target volume at >=Rx dose. Perfect conformality results in a CI=1. With conventional radiotherapy treatment, using treatment planning software, a clinician identifies a dose isocontour for a corresponding VOI for application of a treatment dose (e.g., 2000 cGy).

FIG. 1 illustrates the graphical output of treatment planning software displaying a slice of a CT image a containing pathological anatomy (e.g., tumor, lesion, etc.) region and normal anatomy as a critical region (e.g., internal organ) to be avoided by radiation. The treatment planning software enables the generation of a critical region contour, a target (i.e., pathological anatomy) region contour, and a dose isocontour on the displayed CT slice. Conventionally, a user manually delineates points (e.g., some of the dots on the contour lines of FIG. 1) on the display that is used by the treatment planning software to generate the corresponding contours. While this may seem an easy task, such matching is difficult due to the 3 dimensional nature and irregularities of the pathological and normal anatomies.

Another problem with conventional planning methods is that it may be difficult to achieve the best possible conformality when relying solely on anatomical images on which to base dose constraints because these images provide no information related to current understandings of lesions at the molecular and chemical level. Advances in imaging now offer other types of image modalities to include "functional" information about a lesion, such as biological and mechanistic data. For example, positron emission tomography (PET) images can provide metabolic information about a pathological anatomy such as a lesion. Functional magnetic resonance imaging (fMRI) visualizes changes in the chemical composition of brain areas or changes in the flow of fluids. In PET images, the brightness of different areas of the image may be related to cell density. That is, the greater the brightness in a particular region, the higher the density of lesion cells in that region. It may then be desirable to deliver higher doses of radiation to certain regions of the lesion based on the functional image data. However, some conventional external beam radiation systems may not be able to deliver radiation dose accurately enough to discriminate among such regions within a lesion or tumor, thereby making such identifications unnecessary.

Moreover, despite advances in functional imaging and radiation dose delivery, an operator or physician must go through a number of tedious and time consuming steps to optimize a treatment plan based on combining functional image data with anatomical image data. For example, the physician would have to visually compare a CT image and a PET image of the same VOI, and determine which region of the CT image corresponds to a region of high lesion cell density shown on the PET image based on a visual inspection of different areas of brightness on the PET image. After this determination is made, the physician then would have to manually delineate the visually identified area of greater brightness (that may correspond to a region of high cell density). This process may have to be performed for multiple slices of the CT scan, making the planning process very laborious and time consuming. Moreover, such a manual process that involves the visual inspection of a PET image by a person may cause inaccuracies due to its subjective nature and the fallibility of the observing person.

BRIEF DESCRIPTION OF THE DRAWINGS

The present invention is illustrated by way of example, and not by way of limitation, in the figures of the accompanying drawings.

DETAILED DESCRIPTION

Figure 1:
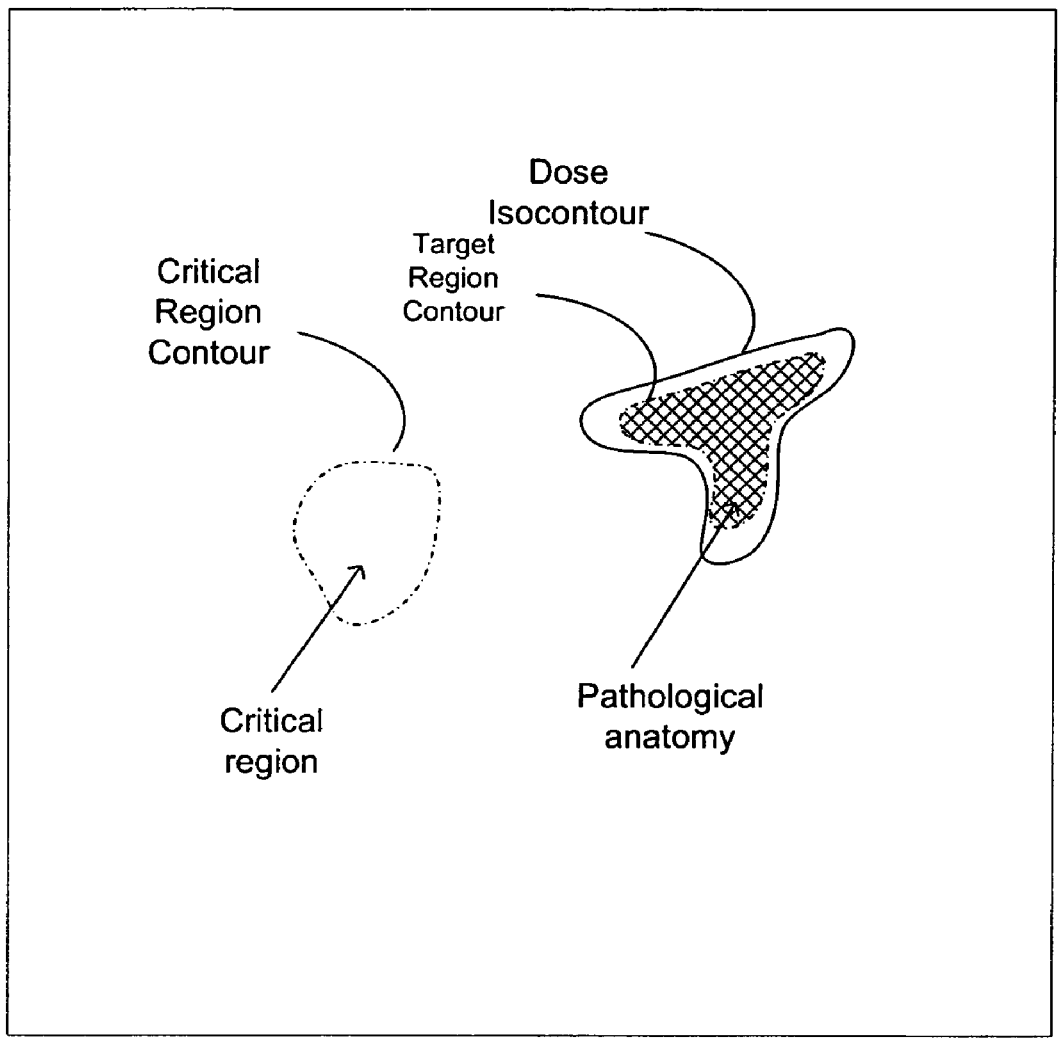
FIG. 1 illustrates a conventional CT image with a delineated critical region and a delineated pathological anatomy region.

In the following description, numerous specific details are set forth such as examples of specific systems, components, methods, etc. in order to provide a thorough understanding of the present invention. It will be apparent, however, to one skilled in the art that these specific details need not be employed to practice the present invention. In other instances, well-known components or methods have not been described in detail in order to avoid unnecessarily obscuring the present invention.

Embodiments of the present invention include various steps, which will be described below. The steps of the present invention may be performed by hardware components or may be embodied in machine-executable instructions, which may be used to cause a general-purpose or special-purpose processor programmed with the instructions to perform the steps. Alternatively, the steps may be performed by a combination of hardware and software.

Embodiments of the present invention may be provided as a computer program product, or software, that may include a machine-readable medium having stored thereon instructions, which may be used to program a computer system (or other electronic devices) to perform a process. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or other type of medium suitable for storing electronic instructions.

Embodiments of the present invention may also be practiced in distributed computing environments where the machine-readable medium is stored on and/or executed by more than one computer system. In addition, the information transferred between computer systems may either be pulled or pushed across the communication medium connecting the computer systems, such as in a remote diagnosis or monitoring system. In remote diagnosis or monitoring, a user may utilize embodiments of the present invention to diagnose or monitor a patient despite the existence of a physical separation between the user and the patient. In addition, the treatment delivery system may be remote from the treatment planning system.

A treatment planning process is described that automatically identifies a region of high cell density based on a corresponding region of high intensity from a functional image such as a PET or single photon emission computed tomography (SPECT) image. The region of high intensity can be constrained to receive a higher dose of radiation relative to other regions of the pathological anatomy having low intensity. For example, it may be advantageous for a radiation treatment plan to direct more radiation in those areas of the lesion with higher cell density, which may exhibit as brighter regions in a PET image. Applying a constant dose to the VOI does not provide enough radiation exposure to regions of the lesion containing higher concentration of lesion cells. Instead of an operator (e.g., a physician or oncologist) having to delineate these higher cell density regions for higher dosing during the inverse planning process manually, the areas of higher cell density are automatically identified by the treatment planning software based on a difference in intensity levels in the pixels of the functional image such as PET, SPECT, functional magnetic resonance imaging (fMRI), etc.

The intensity of the pixels in the functional image can be used as another input to the inverse planning software to customize the radiotherapy process for a patient. In one embodiment, the functional image may be overlaid or registered on the anatomical image. The functional image may be acquired in the same space as the anatomical image (e.g., using a PET/CT scanner). In an alternative embodiment, data from a functional image can be combined with other inputs for inverse planning. For example, the contents of the functional image can be overlaid or fused with an anatomical image (e.g., a CT or MRI).

As such, dose volume constraints for a delineated region from the anatomical image can be combined with dose constraints from the functional image to optimize a treatment plan during inverse planning. Alternatively, the anatomical image may not be required and only the functional image can be used in treatment planning.

In an alternative embodiment, inverse planning can also encompass forward planning. This "mixed" plan can include part of the treatment dose generated using forward planning and part generated by inverse planning. For ease of explanation, examples of inverse planning are described herein in relation to radiotherapy of a lesion in the brain. The methods described herein may also be applied to the treatment of lesions or tumors in other organs or regions of the body where radiation treatment is applicable.

Figure 2:
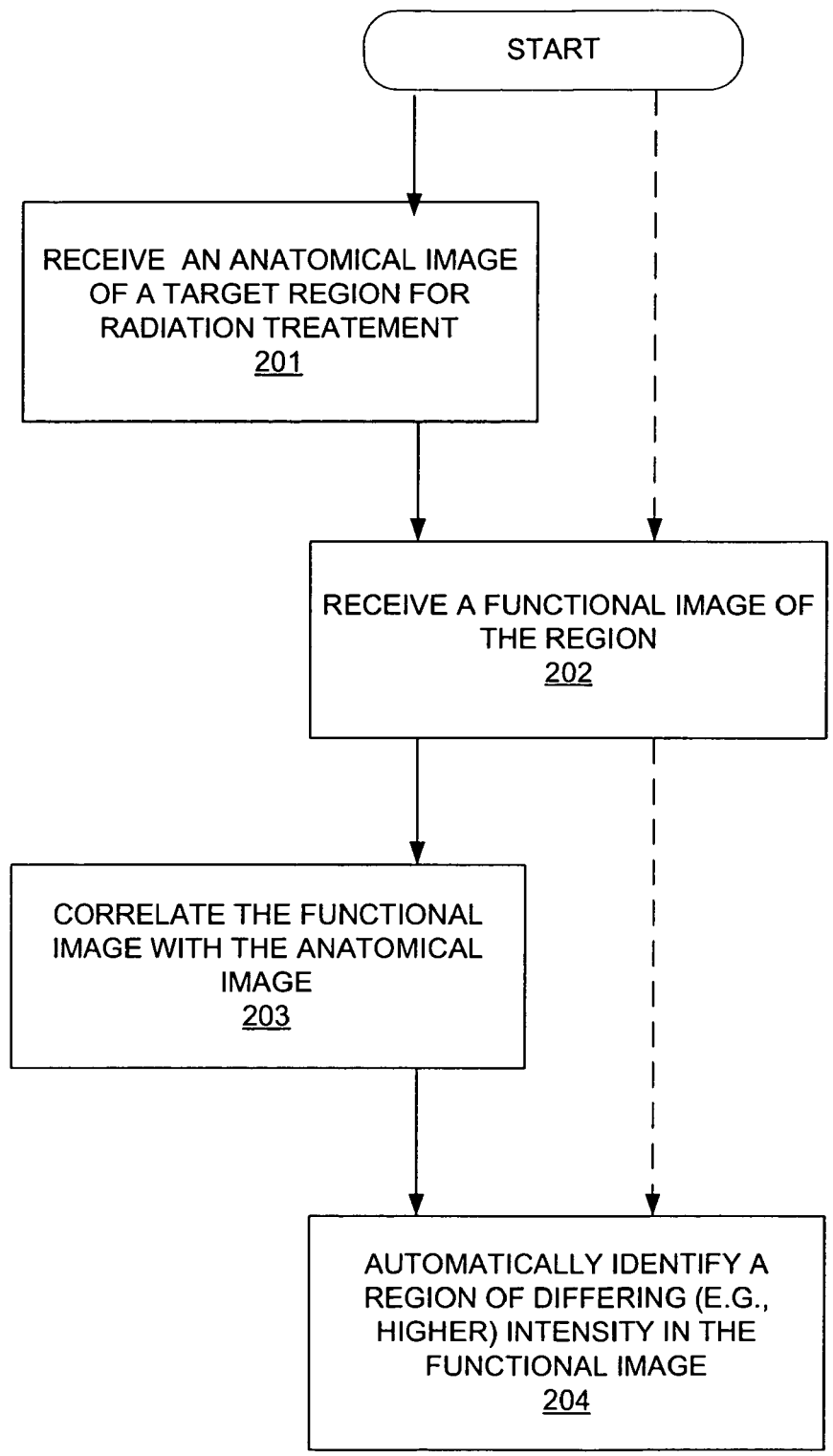
FIG. 2 is a flowchart showing one method of an inverse planning process.

FIG. 2 is a flowchart generally describing one method of inverse planning using inputs from one or more imaging modalities. In one embodiment, the method may begin with receiving an anatomical image of the VOI targeted for radiation treatment, step 201. The anatomical image provides structural representations of the VOI containing the pathological anatomy (e.g., lesion) targeted for treatment, as well as surrounding tissue. For example, in one embodiment, the anatomical image can be a CT image slice. A "slice" of the CT image (i.e., the region of interest) may be examined by the user to manually delineate the target region and the critical region (i.e., healthy tissue), followed by applying a set of dose constraints for each region.

Another image of the VOI using a functional image modality may also be received, step 202. The functional image may of a modality such as a PET image, SPECT image, fMRI image, etc. to provide functional data of the treatment region, step 202. Functional or "biological" images broadly include metabolic, biochemical, physiological categories, and also encompass molecular, genotypic, and phenotypic images. Functional images provide data that cannot be derived from anatomical images. For example, functional imaging of the brain can be used to apply a constraint to avoid critical neurological structures or to target a specific area for treatment.

A functional image may provide data about pathological anatomy such as a lesion that may not be evident from an anatomical image because the cell content within the lesion is not uniform. Certain regions of pathological anatomy such as a lesion can have higher concentrations of cells relative to other regions. In PET images of lesions, regions of high cell activity or metabolism, such as regions cancer cells, are displayed brighter relative to regions of low cell activity. In one method, as described in greater detail below, PET images display differences in cell concentrations by the uptake of sugar molecules.

In one embodiment, the received functional image may be correlated with the anatomical image, step 203 and then additional dose constraints can be applied to the treatment region to further define the dose distribution in inverse planning based on the functional image information about the lesion. In one embodiment, for example, the images may be correlated by overlaying the functional image with the anatomical image. Alternatively, the anatomical and functional images may be correlated in other manners, such as by acquiring the images in the same space (e.g., using a PET/CT scanner) or by registering the functional image with the anatomical images using techniques known in the art.

In step 204, the identification of the higher intensity region in the received functional image of step 202 is performed automatically (not manually performed by the user visually identifying such region on the functional image). An algorithm may be used to automatically identify one or more regions of differing (e.g., higher) intensity within the delineated contour of the target region (pathological anatomy such as a lesion) and generate a corresponding sub-contour (with corresponding dose constraints) for the differing (e.g., higher) intensity region(s) so that such sub-region(s) may receive different radiation dose relative to other region(s) (e.g., of lower intensity). It should be noted that the identification of the higher intensity region is automatically performed in that it does not require (but does not preclude) user intervention in the identification process. For example, the user may be prompted by the treatment planning software to select whether automatic identification is desired; the user may be provided the option of manually assisting the identification; the user may be able to change one or more pixel data values (as discussed in more detail below) during the identification process; etc.

In an alternative embodiment, the method of inverse planning may include only steps 202 and 204 such that the acquisition and receipt of an anatomical image, and its correlation with the functional image, are not performed as indicated by the dashed arrow path in FIG. 2. In such an embodiment, a functional imaging using only a single imaging modality may be acquired and received, and used for both treatment planning purposes and/or automatic identification of the higher intensity region. Although the functional imaging modality is been described above in relation to specific examples of PET, SPECT and fMRI, it should be noted that other imaging modalities may be used. In an alternative embodiment, for example, the functional image modality may be a CT imaging modality where the patient has been injected with a contrast chemical (e.g., a dye such as iodine bound with an enzyme) that bonds to the pathological anatomy in a manner that makes it visible on the CT (e.g., by generating higher intensity in the CT image for higher concentrations of cells relative to other regions).

Figure 3:
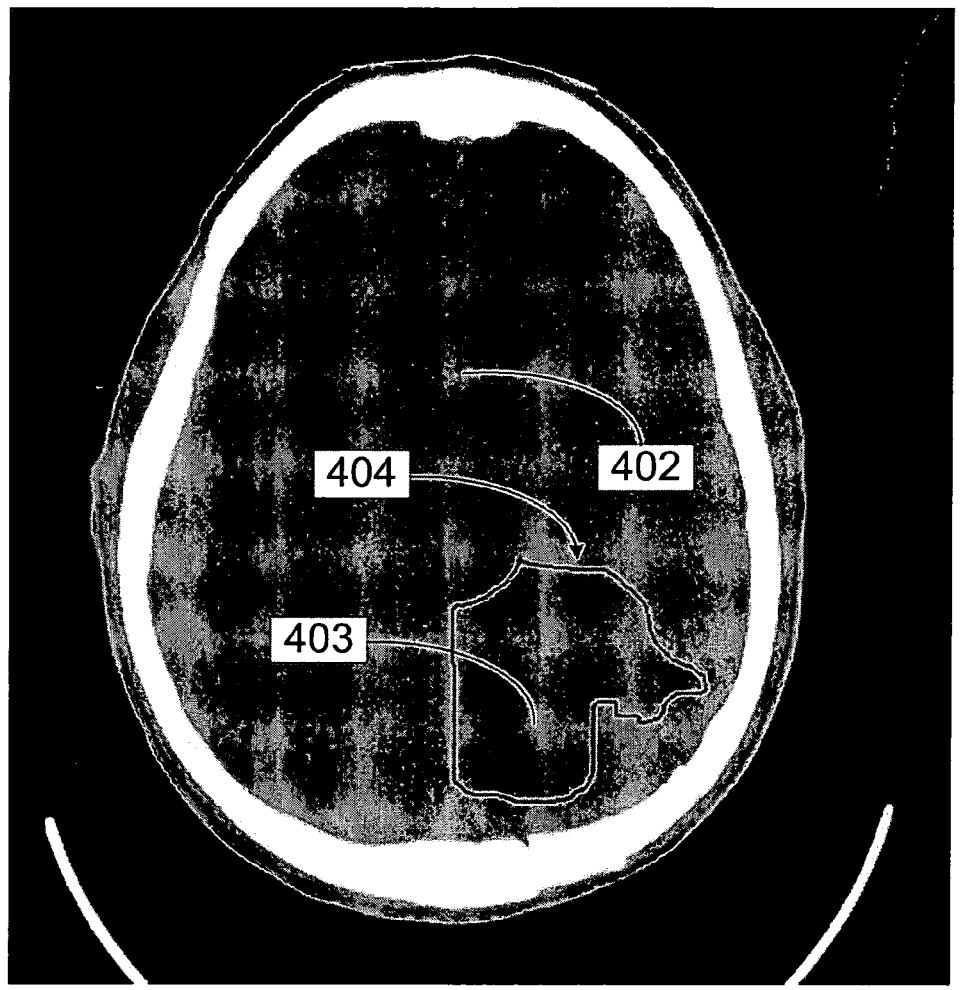
FIG. 3 is a CT image illustrating an axial view of an intra cranial region with a pathological anatomy that has been outlined for reference purposes.

FIG. 3 illustrates a CT image slice 400 of an axial view through an intra cranial region of a patient. CT image 400 is a computer generated image composed of pixels in which varying regions of intensity (e.g., dark region 402) distinguish the various anatomical portions of the brain. CT image 400 may also include a pathological anatomy (e.g., lesion) 403 which as been outlined 404 in FIG. 3 for emphasis).

Figure 4:
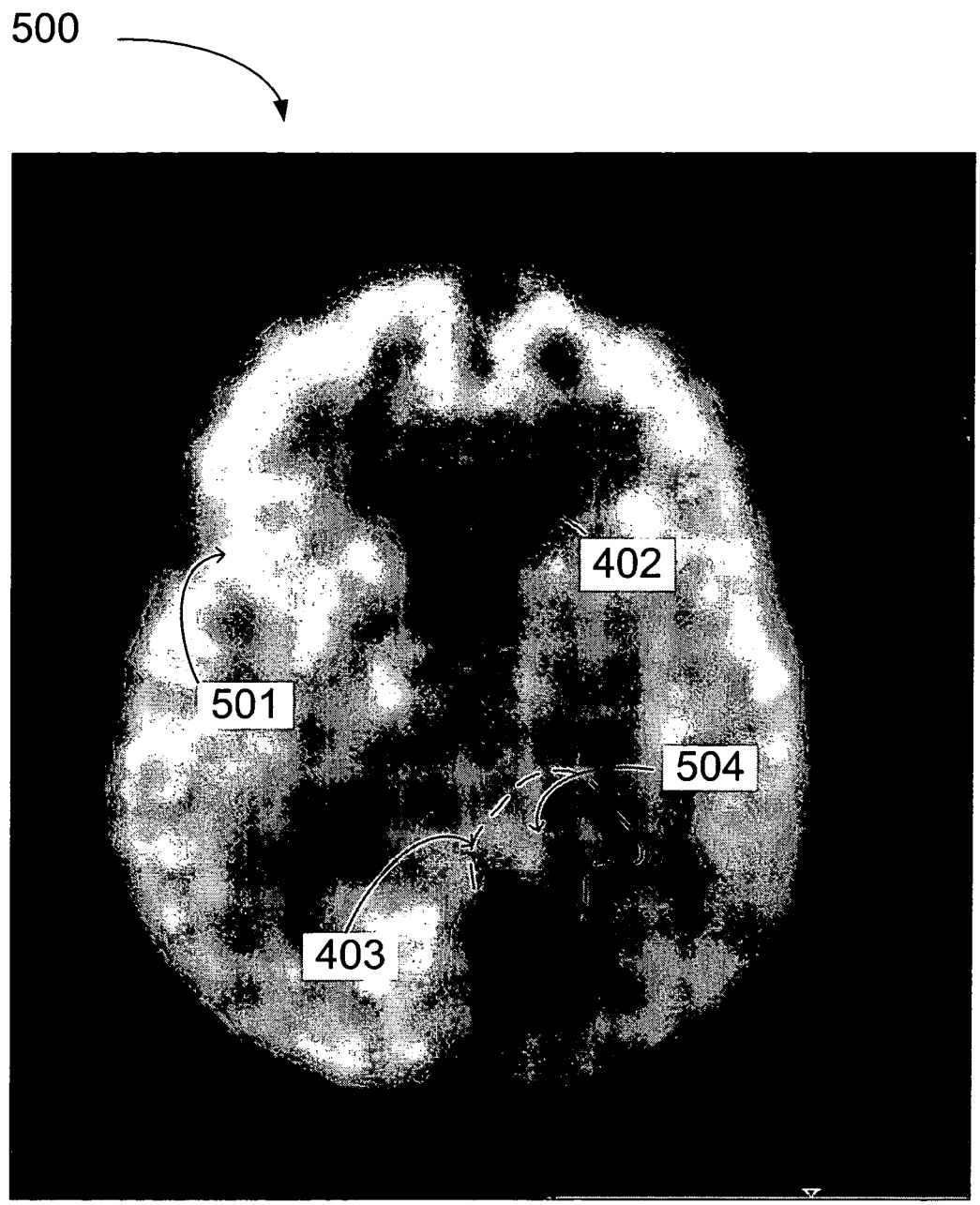
FIG. 4 illustrates a PET image of the axial view of the intra cranial region from FIG. 3.

FIG. 4 illustrates a PET image 400 of the same intra cranial axial view illustrated by CT image 400 of FIG. 3. PET images are considered functional because they provide data relating to the chemical functioning of tissue, as opposed to anatomical or structural data provided by CT images. As briefly described above, a lesion does not necessarily have a uniform distribution of cells within the volume occupied by the lesion. Functional images such as PET scans can provide data relating to the differences in cell density within the lesion volume. Fluorodeoxyglucose (FDG), a radioactive sugar molecule, is used to produce images that demonstrate increased glucose metabolism associated with regions of lesion activity. Because cancer cells grow and divide more rapidly than normal cells, they metabolize more sugar for fuel. This increased activity identifies them as cancer in FDG-PET scanning. For this procedure, the patient is injected with the FDG and lies in a PET camera for the imaging. Areas of activity from PET images are also represented by differences in image intensity, as represented by dark regions 402 and bright regions 501. Especially beneficial is the data shown with respect to tissue activity for lesion 403, which shows a higher intensity region 504, indicating an area of high glucose metabolism, and therefore higher lesion cell content. In one embodiment, the area that corresponds to the higher intensity region 504 on the PET image of FIG. 4 may not be readily visible on the CT image of FIG. 3 (which has been manually outlined on FIG. 3 for reference purposes).

Figure 5:
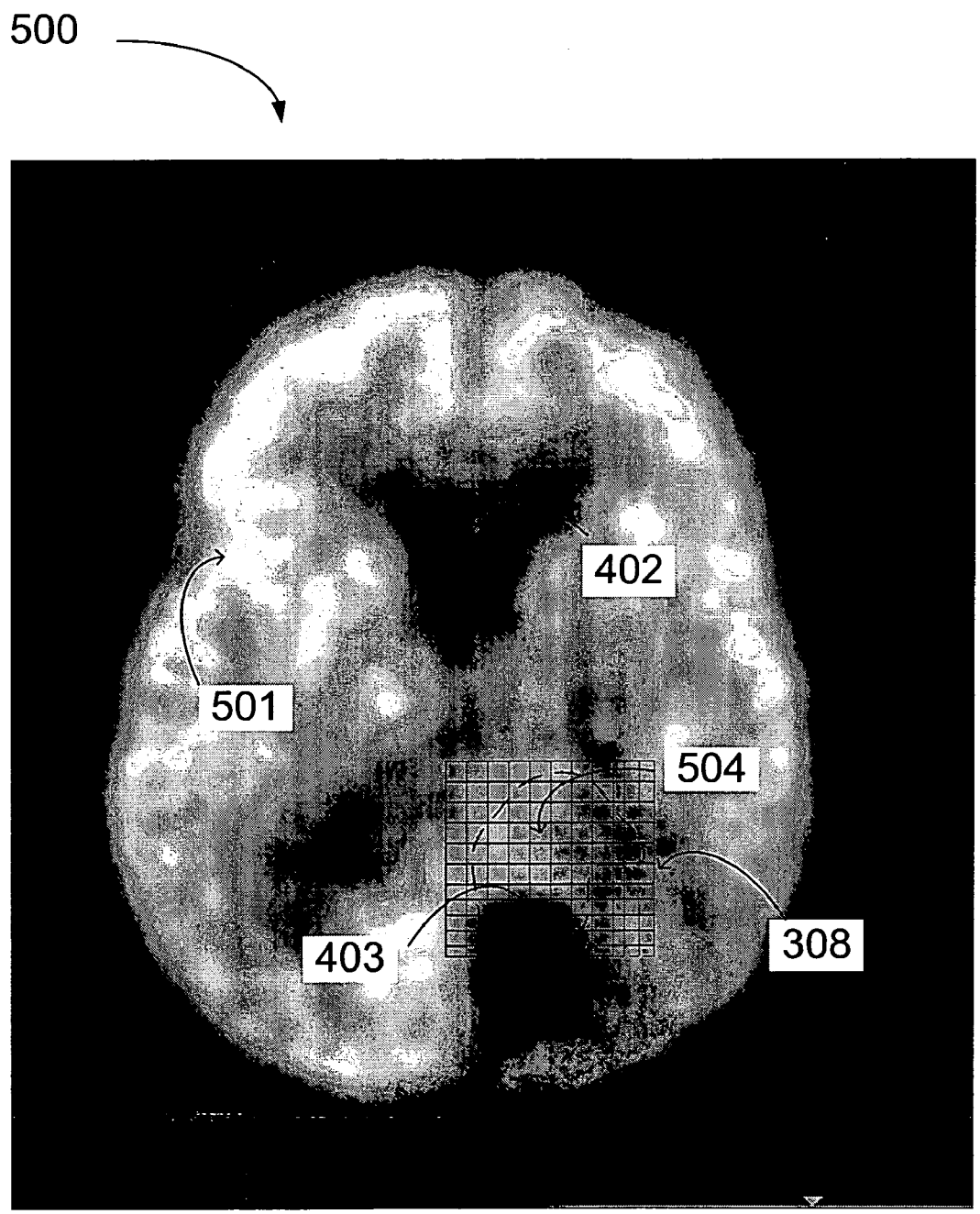
FIG. 5 illustrates one embodiment of pixel intensity data matrix for a functional image.

FIG. 5 illustrates one embodiment of pixel intensity data matrix for a functional image. The data in a functional image 500 may be represented by a matrix, or grid, 308 of the intensity data values of the pixels used to form the image. A portion of the image matrix 308, is only shown in FIG. 5 over the area containing the pathological anatomy for ease of illustration and may actually extend over the entire image. The data value for each pixel in the matrix corresponds to a particular intensity of the image for that pixel. The intensity data values for one or more of the pixels may be used to determine differences in intensity among two or more sub-regions (e.g., within the contour 404 in FIG. 6 for the pathological anatomy). The use of the pixel intensity data values provides a more precise determination of differing cell density regions than the visual brightness of the image as visual "seen" by a person looking at the functional image.

The following algorithm may be used to determine a difference in intensity based on the received intensity data values for each of the pixels in the matrix of a functional image:

```
Set count to zero:
Set pixel intensity total to zero:
For each slice:
    For each PET pixel within the delineated target area:
        Add pixel intensity to the total
        Increase count by 1
    End
End
Set mean target intensity to be pixel intensity total divided by count
For each slice:
    For each PET pixel within the delineated target area:
        If pixel intensity > mean target intensity
            Flag pixel as being part of the high intensity
            area
        Else
            Flag pixel as not being part of the high
            intensity area
        End
    End
End
```

In the above algorithm a threshold value for pixel intensity is calculated, followed by a comparison of each pixel of the delineated area against that threshold value. In particular, the threshold is calculated by summing the intensity values for each pixel of the delineated area, and dividing that total by the total number of pixels. As such, in this embodiment, the mean pixel value corresponds to the threshold pixel value. If the pixel intensity is greater than the threshold value, then that pixel is flagged as being part of the high intensity area. If the pixel intensity is less than the threshold value, then that pixel is flagged as not part of the high intensity area.

Figure 10:
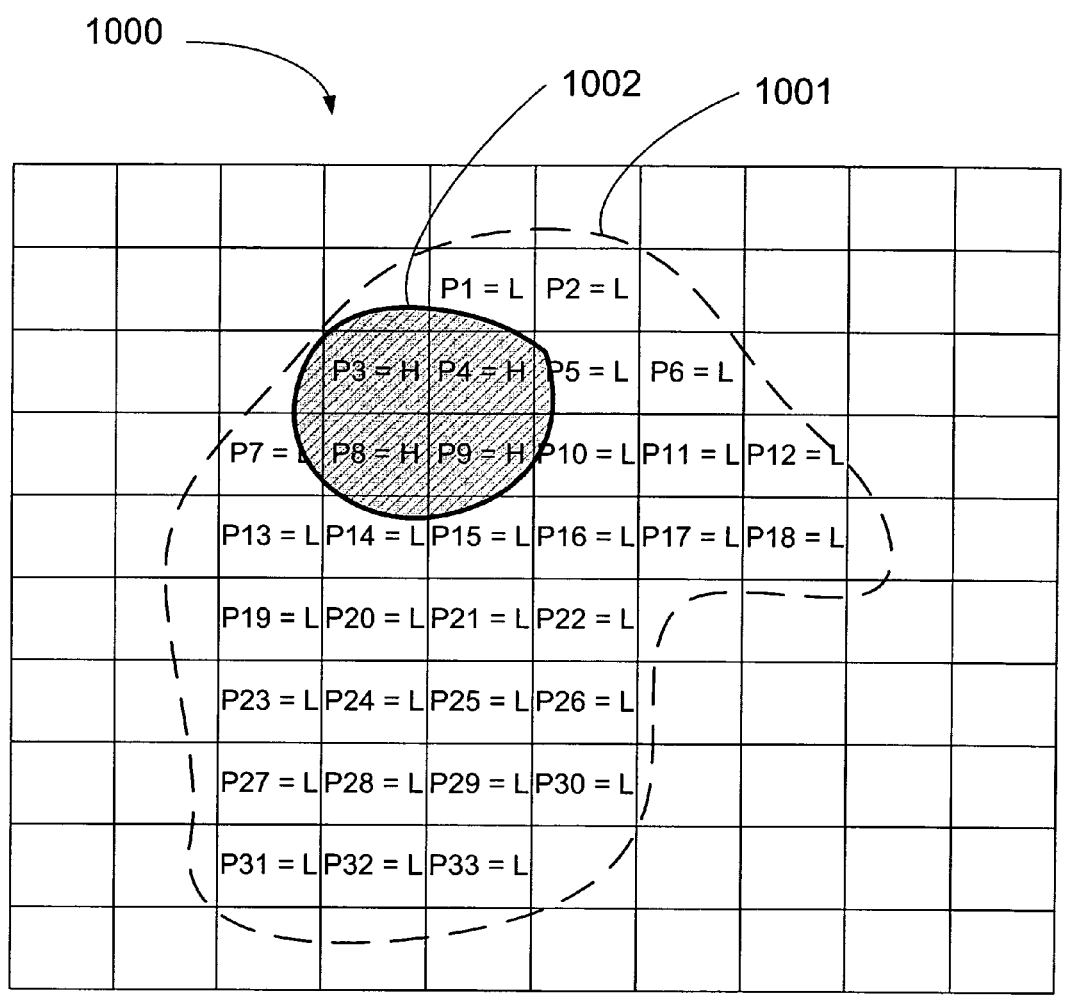
FIG. 10 illustrates the flagging of high intensity pixels for a delineated area.

FIG. 10 is representative FIG. 1000 illustrating the flagging of each pixel for a delineated area, as indicated by segmented line 1001. Delineated area includes 33 pixels (P1 through P33). According to the algorithm, the threshold value, corresponding to the mean target intensity, is calculated by summing the total intensity for P1-P33 and dividing by 33. Four pixels—P3, P4, P8, P9—are flagged as being part of the high intensity area because the pixel intensity value for each of these pixels is greater than the calculated mean target intensity.

In an alternative embodiment, the difference in intensity data values among two or more sub-regions can be determined in other manners, for example, independent of the total intensity value, the number of pixels, and/or a threshold value. For example, all the pixels within delineated area 1001 can be ranked according to increasing intensity value. If P22 had the lowest intensity value and P3 had the highest intensity value, the pixels would be ranked from P22 at one end to P3 at the opposite end. A predetermined number of the highest ranked pixels could then be categorized as being part of the high intensity area. For example, the top ten ranked pixels would be flagged. Alternatively, a predetermined percentage of the top ranked pixels could be flagged as being part of the high intensity area. For example, it could be predetermined that the top 20% of the pixels are flagged. According to the example provided by FIG. 10, pixels P3, P4, P8, and P9 are flagged as being part of a high intensity area because their pixel intensity values are the highest ranked pixels or part of a designated top percentage of pixels. In alternative embodiments, other algorithms including variations of the determining the threshold value may be used in flagging pixels as high intensity.

Figure 6:
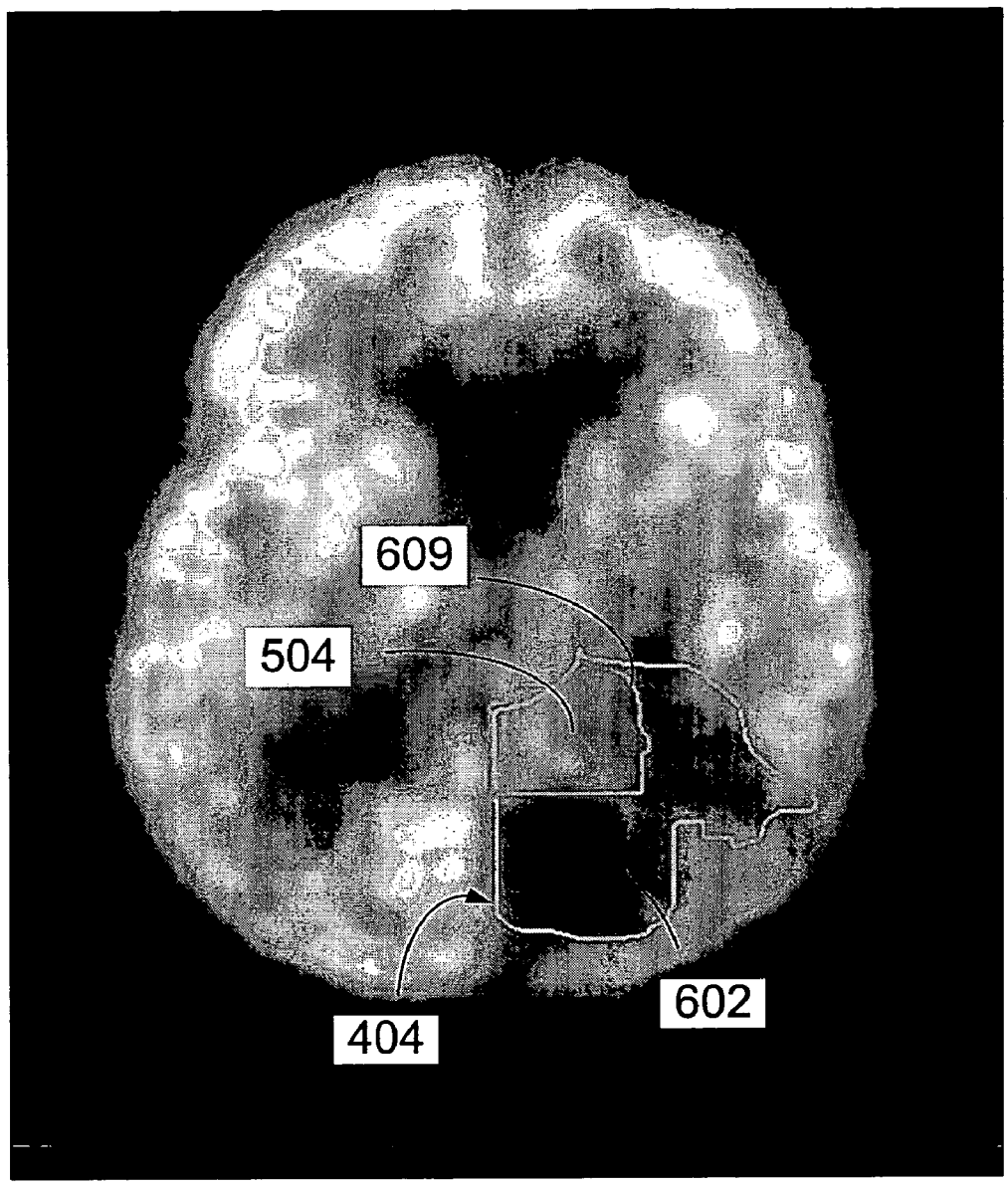
FIG. 6 illustrates the PET image of FIG. 4 with one embodiment of an automatically generated contour of a higher intensity region within the pathological anatomy delineated in the PET image.
Figure 11:
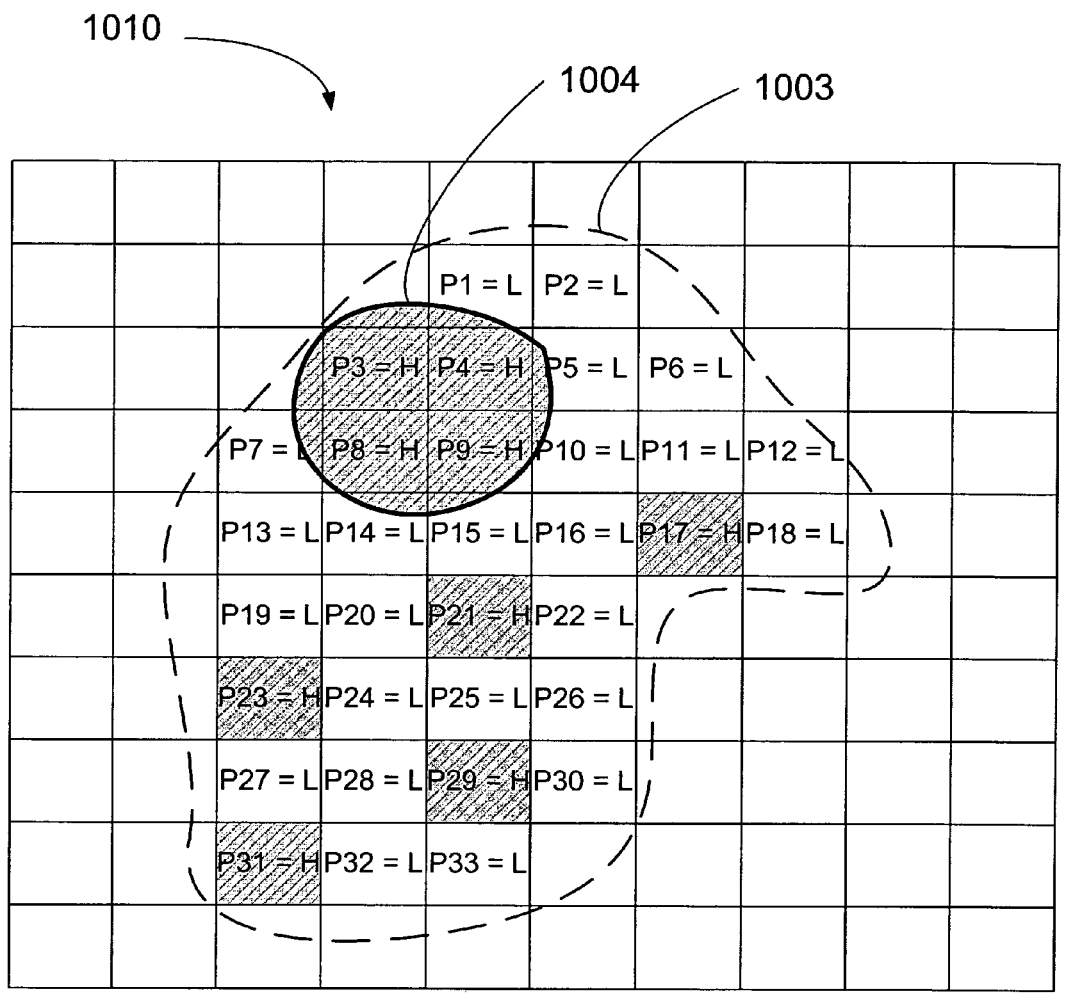
FIG. 11 is another illustration of flagging high intensity pixels for a delineated area.

The different intensity regions identified by the algorithm may be used to generate corresponding contours for each of the different intensity sub-regions automatically, for example, contour 609 of FIG. 6 for higher intensity sub-region 504. Referring again to FIG. 10, a contour 1002 is formed around high intensity pixels P3, P4, P8, and P9. In one embodiment, a contour around a high intensity region is formed automatically if the number of high intensity pixels within the contour is greater than the number of high intensity pixels outside the contour. As illustrated in FIG. 10, there are no high intensity pixels outside of contour 1002, so the group of high intensity pixels has been properly identified. In an alternative embodiment, the automatic contouring of high intensity pixels can be based on pixel proximity. For example, as illustrated in a representative functional scan 1010 of FIG. 11, nine high intensity pixels have been flagged for delineated region 1003. A contour 1004 is generated around pixels P3, P4, P8, and P9 despite the fact that there are additional high intensity pixels outside of contour 1004 (i.e., P17, P21, P23, P29, and P31). As such, a requirement for the generation of contour 1004 can be that one high intensity pixel is adjacent to another high intensity pixel. In other embodiments, variation of pixel proximity or other criteria can be applied to generate a contour automatically. It should be noted that one sub-region having pixels with certain intensity data values could reside within another sub-region.

It should be noted that treatment planning software need not "see" (e.g., by optical image recognition) the function image but, rather, just receive the pixel matrix data in order to automatically identify a difference in the intensity data values between pixels.

In the example of FIG. 6, sub-region 504 is a region having an intensity exceeding a threshold level or value to be considered "high" relative to other regions within the target contour 404. Using inputs corresponding to differences in pixel image intensity, sub-region 504 can be automatically identified and a corresponding contour 609 generated so that a different dose constraint may be applied to sub-region 504 relative to the other sub-regions within target contour 404. A treatment planning system receives the contour 609 for sub-region 504 and its corresponding dose constraints as input and then generates a treatment plan.

The dose distribution is an important parameter in external beam radiation treatment. If a radiation dose were too low in a dense and active sub-region because the radiation is spread over a higher than expected number of cells, then the radiation treatment could be ineffective. If a radiation dose were too high at a particular point in the tissue, the radiation treatment might have negative effects. As such, the intensity data from the functional image (e.g., PET) allows for additional constraints to be applied to an inverse planning system in such a way that conformality of dose to the treatment target is rewarded. For example, the intra-cranial region containing lesion 403 and higher cell density region (corresponding to higher intensity region 504) each receive an appropriate dose distribution within prescribed limits while minimizing the dose and, thereby, damage to surrounding healthy tissue.

One method of applying a dose constraint involves defining an acceptable range for a dose value (Dv) between a minimum dose ($D_{min}$) value and a maximum dose ($D_{max}$) value and can be represented as: $D_{min} \leq Dv \leq D_{max}$. Dose constraints are user-specified and can be applied to manually delineated and automatically generated regions from anatomical and/or functional images. The minimum and maximum dose values are a function of the intensity value (Ip) of the pixels within this region (e.g., matrix 308) and, in one embodiment, may be represented using functions, for example, as $D_{min}(f(Ip)) \leq Dv \leq D_{max}(g(Ip))$, in which $(f(Ip))$ influences minimum dose and $(g(Ip))$ influences maximum dose.

Figure 7A:
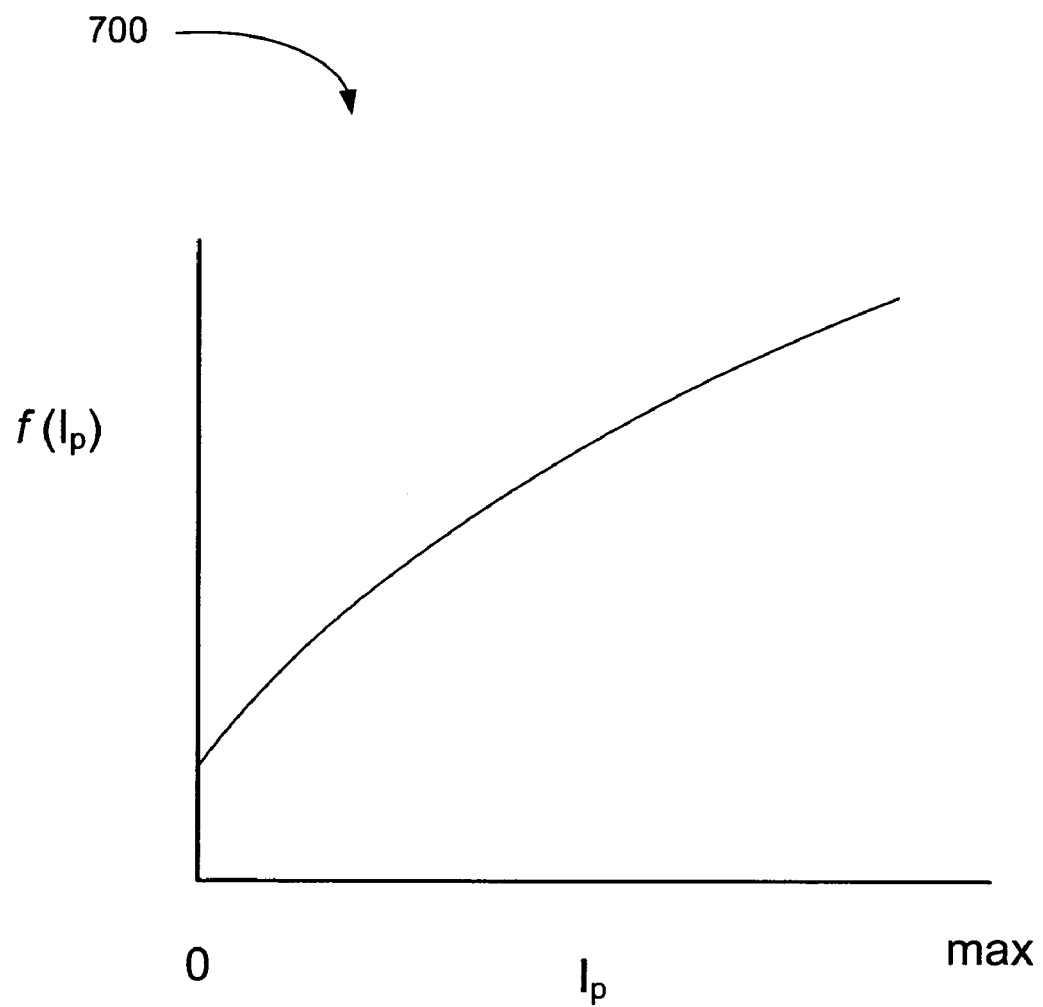
FIG. 7A is a graph showing an acceptable dose minimum as a function of intensity.

FIG. 7A illustrates an exemplary graph 700 showing minimum dose as a function of intensity, such that as the intensity value increases, the minimum dose value of an acceptable dose range increases. Similarly, the maximum dose value also increases as the intensity value increases. Alternatively, other means, such as a look-up table, may be used to determine the dose constraints based on intensity. The generation of a contour and a treatment plan based on the input of contours and dose constraints in known in the art; accordingly, a more detailed description is not provided herein.

Figure 7B:
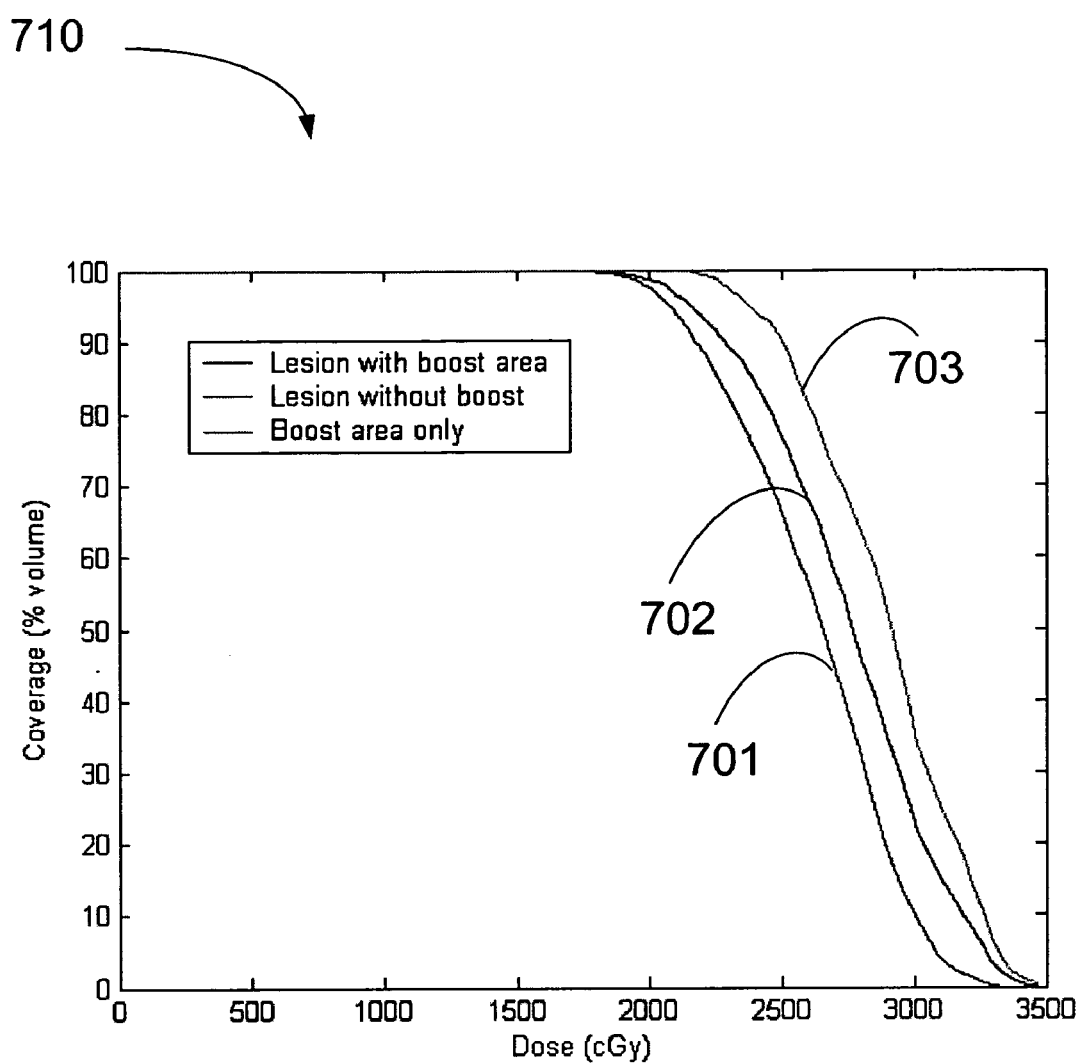
FIG. 7B is a graph showing the DVH for various treatment conditions.

FIG. 7B is a graph 710 illustrating the difference between three example dose volume histograms (DVHs), with each DVH corresponding to conditions with or without functional input from PET image 500. A DVH is a calculated curve that yields the volume percentage receiving a particular radiation dose (in cGy) within the VOI. Ideally, the DVH is a rectangular function, in which the dose is 100 percent of the prescribed dose over the volume of the lesion and zero in non-lesion regions. Curve 701 corresponds to an example calculation from a treatment plan that does not include an input from a functional imaging modality that provides intensity data indicative of cell concentration. Curve 702 corresponds to an example calculation from a treatment plan that includes a boost in dose distribution in sub-region 504. Curve 703 corresponds to an example calculation for sub-region 504 only. Curve 702, which includes a dose boost based on functional image data, has a closer rectangular function relative to curve 701, which does not reflect any dose boost. This difference indicates that a greater amount of lesion cells are exposed and treated based on the dose constraint provided for the higher intensity data. Curve 703 shows the best rectangular function because that coverage is limited only to the boost area of the lesion.

As previously noted, two imaging modalities may not be needed and that a higher intensity region and its corresponding dose constraints can be determined from a single image modality. For example, intensity levels displayed by a PET image for a target lesion can be the sole basis for inverse planning. Moreover, PET images are just one type of functional images that display differences in intensity levels for a target lesion. Single photon emission computed tomography (SPECT), fMRI, and nuclear magnetic resonance (NMR) imaging are other types of functional images that can generate inputs for inverse planning.

Figure 8:
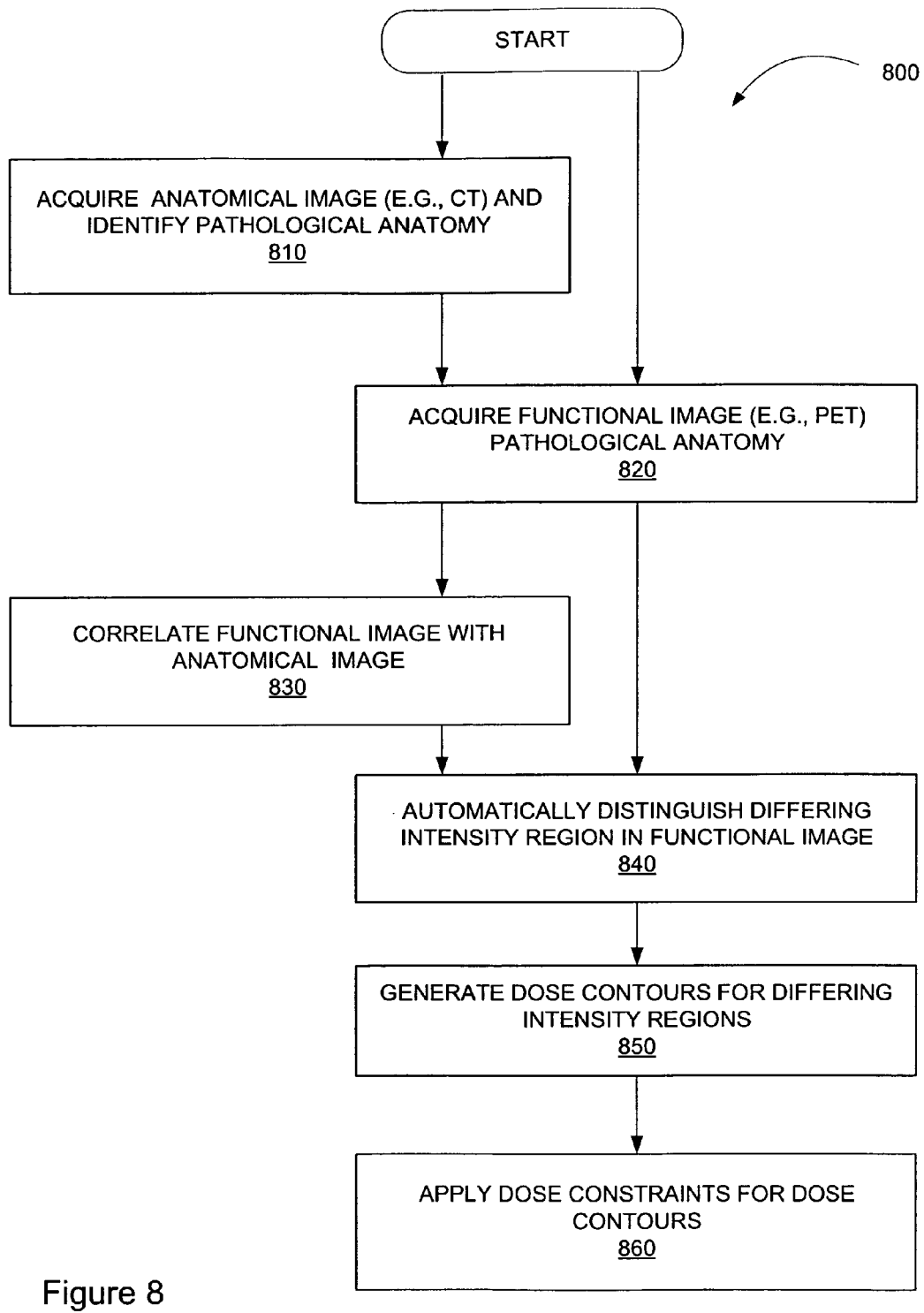
FIG. 8 is a flowchart illustrating one embodiment of a method of inverse treatment planning.

FIG. 8 is a flowchart illustrating one embodiment of a method of inverse treatment planning. Flowchart 800 is described with respect to an example of delivering a radiation dose to a lesion located within the brain of a patient but the method of the present invention is not so limited and may be applied to the delivery of radiation dose to other pathological anatomies in other portions of the patient.

In one embodiment, anatomical data of the lesion is obtained by acquiring an anatomical image (e.g., CT) to form a three-dimensional view of the lesion and the surrounding tissue, step 810. An exemplary CT image is the axial slice of a patient's brain as shown above with respect to CT image 400 of FIG. 3. The CT image shows the location and size of the lesion (e.g., 403) and its surrounding tissue. The lesion region may also be analyzed with functional data from an acquired functional image (e.g., PET), step 820. An exemplary PET image is PET image 500 of FIG. 4. The PET image shows the metabolic activity of the scanned region, and in particular, the degree of cellular activity within various portions of the lesion. Regions of high metabolic activity are depicted as relatively bright regions (e.g., region 504).

In one embodiment, the anatomical (e.g., CT) image and the functional (e.g., PET) image are correlated (e.g., by overlay) with each other, step 830, to combine the data derived from each image modality. Alternatively, no correlation may be performed and no anatomical image need be generated, as previously discussed above.

At step 840, the identification of one or more regions of differing intensity in the functional image is performed automatically, as discussed above. An algorithm is used to automatically identify one or more regions of differing (e.g., higher) intensity within the delineated contour of the lesion and, in step 850, one or more corresponding contours for the differing intensity regions are generated. In step 860, dose constraints may be applied for the generated contours. For example, a higher dose volume constraint can be applied to automatically identified higher intensity region 504 (e.g., the higher cell density region), while a lower dose constraint can be applied to the other areas of lesion 403 (the area outside of contour 609 but within contour 404). Other types of constraints can be applied to organs or otherwise healthy tissue surrounding the target lesion based on the CT image.

Figure 9:
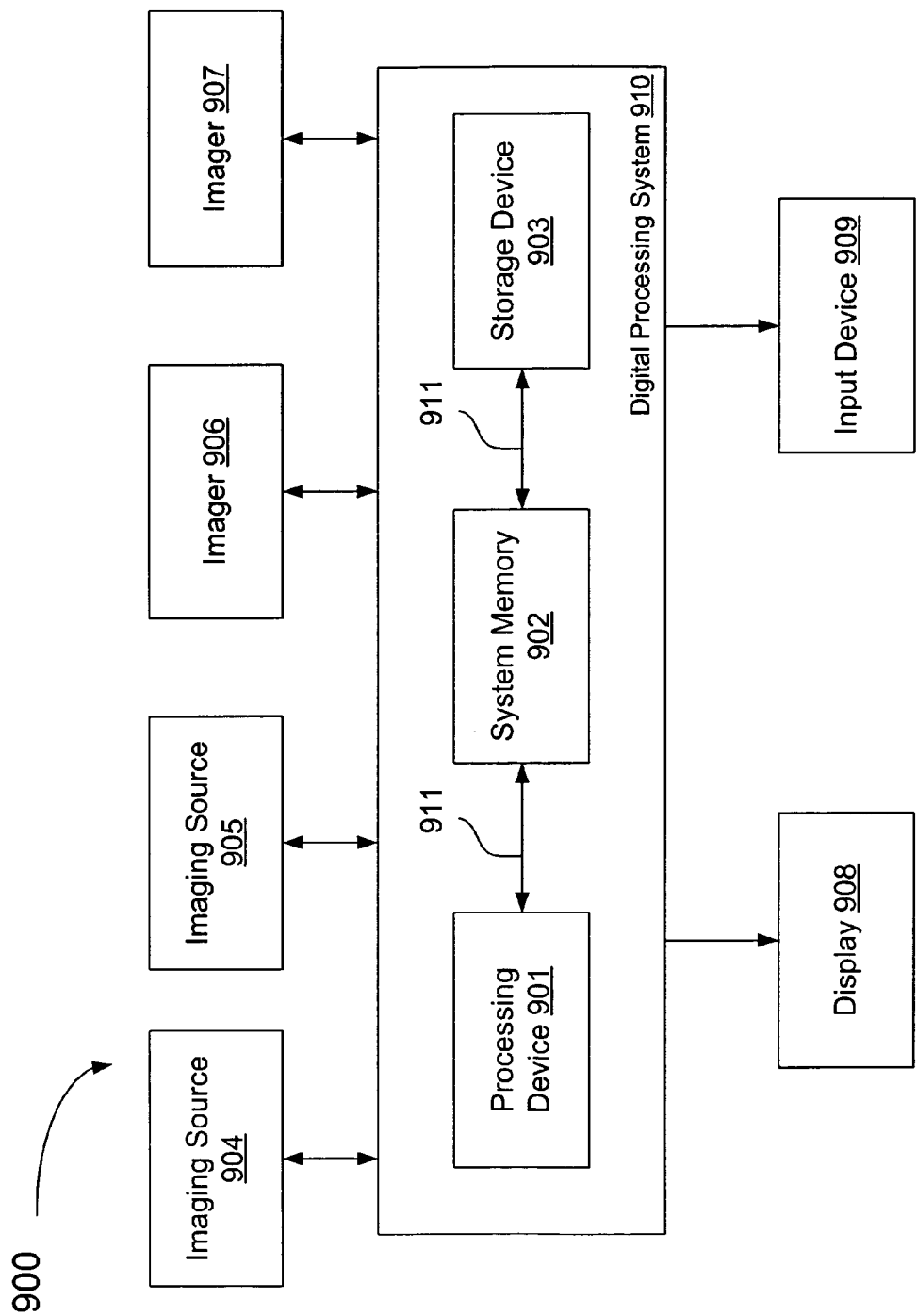
FIG. 9 illustrates a medical diagnostic imaging system implementing one embodiment of the present invention.

FIG. 9 illustrates one embodiment of medical diagnostic imaging and inverse planning system 900 in which features of the present invention may be implemented. The medical diagnostic imaging system 900 is discussed below at times in relation to anatomical and functional imaging modalities (e.g., CT and PET) only for ease of explanation. However, other imaging modalities may be used as previously mentioned.

Medical diagnostic imaging system 900 includes one or more imaging sources 904, 905 to generate a beam (e.g., kilovoltage x-rays, mega voltage x-rays, ultrasound, MRI, PET, etc.) and one or more corresponding imagers 905, 906 to detect and receive the beam generated by imaging sources 904, 905. For example, imager 905 can correspond to a CT imager and imager 906 can correspond to a PET imager. Imaging sources 904, 905 and the imagers 905, 906 are coupled to a digital processing system 910 to control the imaging operation. Digital processing system 910 includes a bus or other means 911 for transferring data among components of digital processing system 910. Digital processing system 910 also includes a processing device 901. Processing device 901 may represent one or more general-purpose processors (e.g., a microprocessor), special purpose processor such as a digital signal processor (DSP) or other type of device such as a controller or field programmable gate array (FPGA). Processing device 901 may be configured to execute the instructions for performing the operations and steps discussed herein. In particular, processing device 901 may be configured to execute instructions to automatically delineate and constrain regions of high intensity (e.g., sub-region 305) in the target region to guide dose distribution. For example, sub-region 305 can be automatically adjusted to receive a higher dose of radiation and have a bigger acceptable dose range.

Digital processing system 910 may also include system memory 902 that may include a random access memory (RAM), or other dynamic storage device, coupled to bus 911 for storing information and instructions to be executed by processing device 910. System memory 902 also may be used for storing temporary variables or other intermediate information during execution of instructions by processing device 910. System memory 902 may also include a read only memory (ROM) and/or other static storage device coupled to bus 911 for storing static information and instructions for processing device 910.

A storage device 903 represents one or more storage devices (e.g., a magnetic disk drive or optical disk drive) coupled to bus 911 for storing information and instructions. Storage device 903 may be used for storing instructions for performing the steps discussed herein.

Digital processing system 910 may also be coupled to a display device 907, such as a cathode ray tube (CRT) or liquid crystal display (LCD), for displaying information (e.g., three-dimensional representation of the VOI) to the user. An input device 908, such as a keyboard, may be coupled to digital processing system 910 for communicating information and/or command selections to processing device 910. One or more other user input devices, such as a mouse, a trackball, or cursor direction keys for communicating direction information and command selections to processing device 910 and for controlling cursor movement on display 907 may also be used.

Digital processing system 910 represents only one example of a system, which may have many different configurations and architectures, and which may be employed with the present invention. For example, some systems often have multiple buses, such as a peripheral bus, a dedicated cache bus, etc.

One or more of the components of digital processing system 910 may form a treatment planning system. The treatment planning system may share its database (e.g., stored in storage device 903) with a treatment delivery system, so that it is not necessary to export from the treatment planning system prior to treatment delivery. The treatment planning system may also include MIRIT (Medical Image Review and Import Tool) to support DICOM import (so images can be fused and targets delineated on different systems and then imported into the treatment planning system for planning and dose calculations), expanded image fusion capabilities that allow the user to plan and view isodose distributions on any one of various imaging modalities (e.g., MRI, CT, PET, etc.).

In one embodiment, the treatment delivery system may be a frame-less robotic based linear accelerator (LINAC) radiosurgery system, such as the CyberKnife® system developed by Accuray, Inc. of California. In such a system, the LINAC is mounted on the end of a robotic arm having multiple (e.g., 5 or more) degrees of freedom in order to position the LINAC to irradiate the pathological anatomy with beams delivered from many angles in an operating volume (e.g., sphere) around the patient. Treatment may involve beam paths with a single isocenter, multiple isocenters, or with a non-isocentric approach (i.e., the beams need only intersect with the pathological target volume and do not necessarily converge on a single point, or isocenter, within the target). Treatment can be delivered in either a single session (mono-fraction) or in a small number of sessions (hypo-fractionation) as determined during treatment planning.

Alternatively, another type of treatment delivery systems may be used, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. In the IMRT planning, the optimization algorithm of selects subsets of the main beam and determines the amount of time for which the subset of beams should be exposed, so that the dose constraints are best met.

In another embodiment, yet other types of treatment delivery systems may be used, for example, a stereotactic frame system such as the GammaKnife®, available from Elekta of Sweden. With such a system, the forward planning optimization algorithm (also referred to as a sphere packing algorithm) of the treatment plan determines the selection and dose weighting assigned to a group of beams forming isocenters in order to best meet provided dose constraints.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
receiving a functional image including a first region of a pathological anatomy comprising first pixels and a second region of the pathological anatomy comprising second pixels, each of the first and second pixels having a corresponding intensity data value; and
automatically distinguishing between the first region and the second region based on a difference between the intensity data values of the first and second pixels, wherein automatically distinguishing comprises:
comparing the intensity data values of the second pixels against the threshold intensity value;
determining that the intensity data values of the second pixels are less than the threshold intensity value;
calculating a total pixel count and a total intensity, from the first and second pixels, for the pathological anatomy from a slice of the functional image;
setting a mean target intensity based on the total intensity divided by the total pixel count; and
flagging a pixel as being part of a high intensity area if the corresponding intensity value is greater than the mean target intensity.

2. A method, comprising:
receiving a functional image including a first region of a pathological anatomy comprising first pixels and a second region of the pathological anatomy comprising second pixels, each of the first and second pixels having a corresponding intensity data value; and
automatically distinguishing between the first region and the second region based on a difference between the intensity data values of the first and second pixels, wherein automatically distinguishing comprises:

ranking the first pixels and the second pixels from a lowest intensity data value to a highest intensity data value;
assigning a threshold intensity value that is between the lowest intensity value and the highest intensity value; and
flagging a pixel as part of a high intensity area if greater than the threshold intensity value.

3. A computer readable medium having instructions thereon, which when executed by a processor, cause the processor to perform the following comprising:
receiving a functional image including a first region of a pathological anatomy comprising first pixels and a second region of the pathological anatomy comprising second pixels, each of the first and second pixels having a corresponding intensity data value; and
automatically distinguishing between the first region and the second region based on a difference between the intensity data values of the first and second pixels, wherein automatically distinguishing comprises:
comparing the intensity data values of the second pixels against the threshold intensity value;
determining that the intensity data values of the second pixels are less than the threshold intensity value;
calculating a total pixel count and a total intensity, from the first and second pixels, for the pathological anatomy from a slice of the functional image;
setting a mean target intensity based on the total intensity divided by the total pixel count; and
flagging a pixel as being part of a high intensity area if the corresponding intensity value is greater than the mean target intensity.

4. An apparatus, comprising:
means for acquiring a functional image; and
means for automatically identifying a region of differing intensity relative to other regions in the functional image, wherein means for identifying further comprises:
means for calculating a total pixel count and a total intensity for a pathological anatomy from a slice of the functional image;
means for setting a mean target intensity based on the total intensity divided by the total pixel count; and
means for flagging a pixel as being part of a high intensity area if the corresponding intensity value is greater than the mean target intensity.

* * * * *